(12) United States Patent
Hatakeyama

(10) Patent No.: US 10,933,092 B2
(45) Date of Patent: Mar. 2, 2021

(54) TOPICAL DERMATOLOGICAL COMPOSITION

(71) Applicant: TEIKOKU CO., LTD., Minoo (JP)

(72) Inventor: Kenichiro Hatakeyama, Minoo (JP)

(73) Assignee: TEIKOKU CO., LTD., Minoo (JP)

( * ) Notice: Subject to any disclaimer, the term of this patent is extended or adjusted under 35 U.S.C. 154(b) by 0 days.

(21) Appl. No.: 16/643,640

(22) PCT Filed: Aug. 28, 2018

(86) PCT No.: PCT/JP2018/031635
§ 371 (c)(1),
(2) Date: Mar. 2, 2020

(87) PCT Pub. No.: WO2019/044788
PCT Pub. Date: Mar. 7, 2019

(65) Prior Publication Data
US 2020/0376024 A1   Dec. 3, 2020

(30) Foreign Application Priority Data

Sep. 4, 2017 (JP) .............................. JP2017-169233

(51) Int. Cl.
| | | |
|---|---|---|
| A61K 33/32 | (2006.01) | |
| A61K 33/26 | (2006.01) | |
| A61K 9/00 | (2006.01) | |
| A61K 33/12 | (2006.01) | |
| A61K 33/30 | (2006.01) | |

(52) U.S. Cl.
CPC ............ *A61K 33/32* (2013.01); *A61K 9/0014* (2013.01); *A61K 33/12* (2013.01); *A61K 33/26* (2013.01); *A61K 33/30* (2013.01)

(58) Field of Classification Search
CPC ........ A61K 33/32; A61K 33/12; A61K 33/26; A61K 9/0014; A61K 33/30
See application file for complete search history.

(56) References Cited

U.S. PATENT DOCUMENTS

| | | | | |
|---|---|---|---|---|
| 4,857,306 A | * | 8/1989 | Roller | A61K 8/19 424/63 |
| 2009/0297628 A1 | * | 12/2009 | Launay | A61K 8/19 424/647 |
| 2011/0129453 A1 | * | 6/2011 | Harripersad | A61K 8/19 424/94.1 |
| 2014/0200193 A1 | * | 7/2014 | Cueto Garcia | A61L 15/58 514/41 |

FOREIGN PATENT DOCUMENTS

| | | |
|---|---|---|
| CN | 104784071 A | 7/2015 |
| JP | 2004100116 A | 4/2004 |

OTHER PUBLICATIONS

Eng. Translated CN 104784071, Jul. 2015.*
CN 106619153 A, Eng. Translation, Jul. 2015.*
CN 106619153 A, ng. Translation, Jul. 2009.*
KR 20090073622 A, Eng. Translation, May 2017.*
Eng. Trans opf Tables of CN 106619153 A, Jul. 2015.*
International Search Report issued in PCT/JP2018/031635 dated Oct. 2, 2018.

* cited by examiner

*Primary Examiner* — Blessing M Fubara
(74) *Attorney, Agent, or Firm* — Heslin Rothenberg Farley & Mesiti P.C.

(57) ABSTRACT

An object is to provide an external composition for skin capable of easily enhancing body balance ability even for ordinary people such as housewives, students, middle-aged and mature-aged males and females, and elderly persons who do not aggressively exercise on a routine basis other than athletes. The object has been solved by an external composition for skin including a rhodochrosite extract extracted from rhodochrosite with water, a hematite extract extracted from hematite with water, a smithsonite extract extracted from smithsonite with water, and an olivine extract extracted from olivine with water, and the like.

4 Claims, 6 Drawing Sheets

TOPICAL DERMATOLOGICAL COMPOSITION

CROSS REFERENCE TO RELATED APPLICATIONS

This application is the National Phase filing under 35 U.S.C. § 371 of International Application No.: PCT/JP2018/031635, filed on Aug. 28, 2018, which claims priority to Japanese Application No.: 2017-169233, filed on Sep. 4, 2017. The contents of each of the prior applications are hereby incorporated by reference herein in their entirety.

TECHNICAL FIELD

The present invention relates to an external composition for skin which is contacted with a body such as a finger, a hand, an arm, a foot, a leg, and a body trunk through spraying, application, or the like for regulating body balance.

BACKGROUND ART

Recently, it has been becoming important to train muscles of a body trunk serving as starting points of movements of extremities when hands, feet, and the like are moved through an action performed in sports such as soccer, tennis, and baseball, and body trunk trainings have started to be actively introduced. Such body trunk trainings enable force and energy generated by using, for example, a leg to effectively connect movements of an arm or a hand through a body trunk.

Then, among body trunk trainings, body balance ability, which becomes important during play, can be also enhanced by a training in which a body is purposely kept under an unstable state conducted by combining a balance board, a balance ball, and the like to train also muscles positioned in a body trunk including various muscles.

Such a body trunk training for enhancing body balance ability has been already widely known through books, videos, websites, and the like and has been spreading to housewives, students, elderly persons, and the like besides athletes.

For example, Patent Literature 1 discloses clothes such as tights capable of obtaining enhanced body balance and body-supporting power by wearing the clothes and capable of maximally bringing out exercise effect.

CITATION LIST

Patent Literature

Patent Literature 1
Japanese Patent Laid-Open No. 2004-100116

SUMMARY OF INVENTION

Technical Problem

However, a certain training time is required to be taken for conventionally known body trunk trainings. Therefore, conventionally known body trunk trainings are not easy for ordinary people such as housewives, students, middle-aged and mature-aged males and females, and elderly persons who do not aggressively exercise on a routine basis other than athletes and have a problem of not being enough to satisfy needs of such ordinary people to enhance their body balance ability.

In addition, the clothes described in Patent Literature 1 are inconvenient because they are required to be worn at all times and cannot be worn depending on the kind of sports.

In view of the above, the present invention aims at providing an external composition for skin capable of easily enhancing body balance ability even for ordinary people such as housewives, students, middle-aged and mature-aged males and females, and elderly persons who do not aggressively exercise on a routine basis other than athletes regardless of the kind of sports.

Solution to Problem

That is, the present invention is an external composition for skin comprising a rhodochrosite extract extracted from rhodochrosite with water, a hematite extract extracted from hematite with water, a smithsonite extract extracted from smithsonite with water, and an olivine extract extracted from olivine with water.

Further, the present invention is the external composition for skin according to the above [0010], wherein a content of manganese in the rhodochrosite extract is 1.0 to 3.5 g/L, a content of iron in the hematite extract is 0.2 to 1.2 g/100 g, a content of zinc in the smithsonite extract is 1.2 to 2.5 g/L, and a content of magnesium in the olivine extract is 2.0 to 4.5 g/L.

Further, the present invention is the external composition for skin according to the above [0011], comprising 0.2% to 0.5% by weight of the rhodochrosite extract, 0.2% to 0.5% by weight of the hematite extract, 0.2% to 0.5% by weight of the smithsonite extract, and 0.2% to 0.5% by weight of the olivine extract.

Advantageous Effect of Invention

According to the present invention, ordinary people such as housewives, students, middle-aged and mature-aged males and females, and elderly persons who do not aggressively exercise on a routine basis other than athletes can also easily enhance their body balance ability.

DESCRIPTION OF EMBODIMENTS

Figure 1:
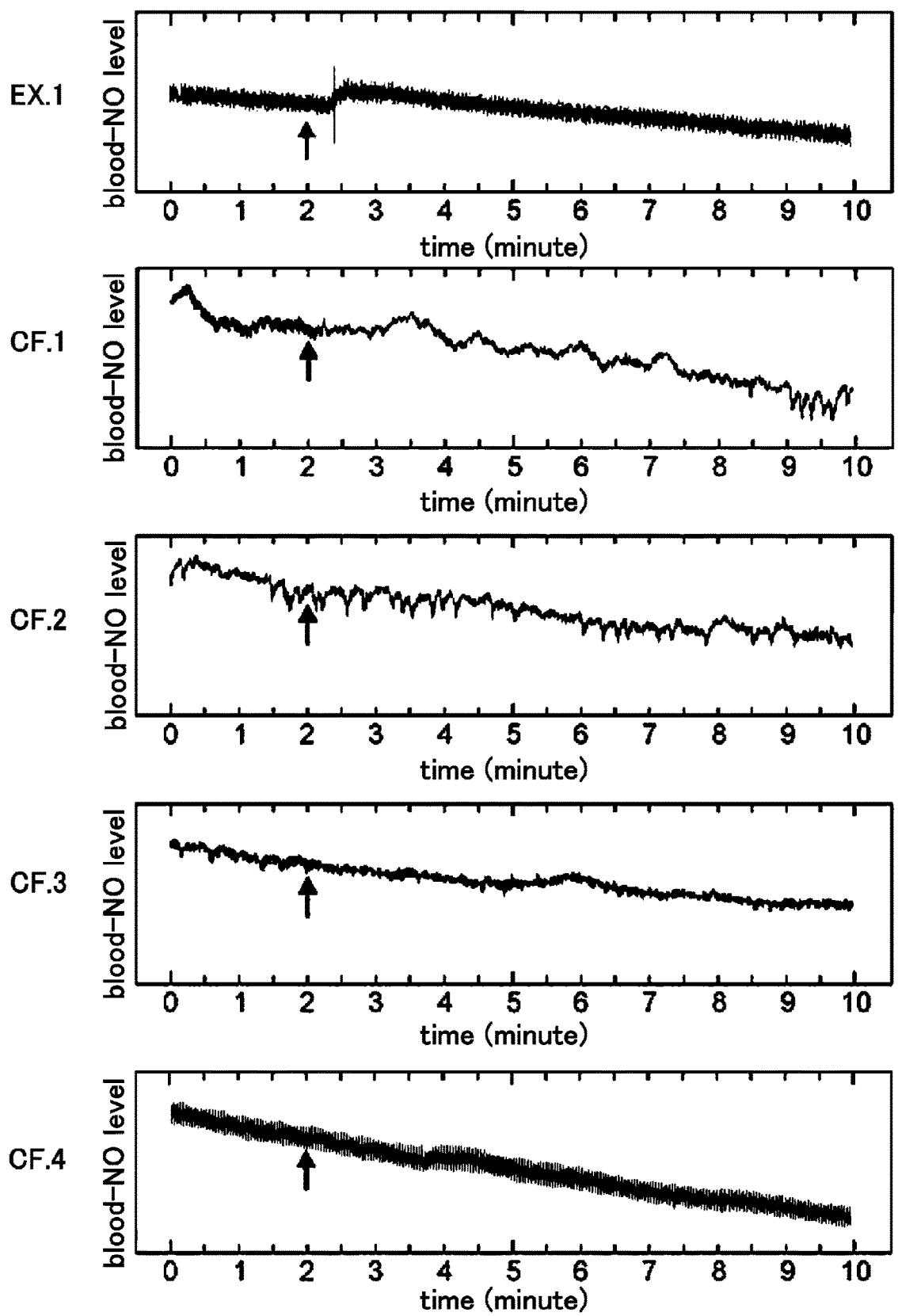
FIG. 1 shows charts showing test results of measurements of amounts of nitric oxide (NO) in blood of rats with which cloths impregnated with compositions of Example 1 and Comparative Examples 1 to 4 respectively are contacted.

Hereinafter, embodiments relating to an external composition for skin of the present invention are described in detail. When a representation representing a range is given in the description, the upper limit and the lower limit are included in the range.

A rhodochrosite extract is an extract obtained from rhodochrosite, which is a carbonate mineral of manganese, through extraction with water. More specifically, the rhodochrosite extract is an aqueous solution which is a filtrate obtained by pulverizing raw rhodochrosite to approximately have a predetermined particle diameter, adding water and optionally an acidic compound, a solubilizing agent, and an antiseptic to the pulverized matter followed by stirring and mixing, and subsequently filtering the resulting mixture with a filter or the like. In addition to water at an ordinary temperature of about 20 to 30° C., cold water at a temperature lower than ordinary temperature and warm water and hot water at a temperature higher than ordinary temperature on the contrary can be used as water for extraction.

Then, a content of manganese in the obtained rhodochrosite extract is preferably 1.0 to 3.5 g/L and more preferably 1.5 to 3.0 g/L. When the content of manganese in the rhodochrosite extract is within the above range, body balance ability can be enhanced by virtue of synergy with another extract without producing precipitates even when the external composition for skin of the present invention is stored for a long time of several months, several years, or the like in its liquid state. The content of manganese is calculated according to a method in which a calibration curve is prepared from a manganese standard solution with a known concentration using atomic absorption spectrometry and a quantity is determined by the calibration curve method, or the like.

Further, a content of the rhodochrosite extract in the external composition for skin of the present invention is preferably 0.2 to 0.5% by weight and more preferably 0.3 to 0.4% by weight. When the content of the rhodochrosite extract in the external composition for skin is within the above range, body balance ability can be enhanced.

In addition, while the rhodochrosite extract can also be obtained by conducting the above-described extraction operations by one's own, a commercially available product can also be purchased. As a commercially available product, RHODO'LITE 2 (manufactured by IKEDA CORPORATION) can be available, for example.

A hematite extract is an extract obtained from hematite, which is a mineral of iron oxide, through extraction with water. More specifically, the hematite extract is an aqueous solution which is a filtrate obtained by pulverizing raw hematite to approximately have a predetermined particle diameter, adding water and optionally an acidic compound, a solubilizing agent, and an antiseptic to the pulverized matter followed by stirring and mixing, and subsequently filtering the resulting mixture with a filter or the like. In addition to water at an ordinary temperature of about 20 to 30° C., cold water at a temperature lower than ordinary temperature and warm water and hot water at a temperature higher than ordinary temperature on the contrary can be used as water for extraction.

Then, a content of iron in the obtained hematite extract is preferably 0.2 to 1.2 g/100 g and more preferably 0.5 to 0.9 g/100 g. When the content of iron in the hematite extract is within the above range, body balance ability can be enhanced by virtue of synergy with another extract without producing precipitates even when the external composition for skin of the present invention is stored for a long time of several months, several years, or the like in its liquid state. The content of iron is calculated according to a method in which a calibration curve is prepared from an iron standard solution with a known concentration using atomic absorption spectrometry and a quantity is determined by the calibration curve method, or the like.

Further, a content of the hematite extract in the external composition for skin of the present invention is preferably 0.2 to 0.5% by weight and more preferably 0.3 to 0.4% by weight. When the content of the hematite extract in the external composition for skin is within the above range, body balance ability can be enhanced.

In addition, while the hematite extract can also be obtained by conducting the above-described extraction operations by one's own, a commercially available product can also be purchased. As a commercially available product, HEMA'TITE (manufactured by IKEDA CORPORATION) can be available, for example.

A smithsonite extract is an extract obtained from smithsonite, which is a carbonate mineral of zinc, through extraction with water. More specifically, the smithsonite extract is an aqueous solution obtained by pulverizing raw smithsonite to approximately have a predetermined particle diameter, adding water and optionally an acidic compound, a solubilizing agent, and an antiseptic to the pulverized matter followed by stirring and mixing, subsequently filtering the resulting mixture with a filter or the like to obtain a filtrate, and optionally irradiating the filtrate with a predetermined amount of a gamma ray. In addition to water at an ordinary temperature of about 20 to 30° C., cold water at a temperature lower than ordinary temperature and warm water and hot water at a temperature higher than ordinary temperature on the contrary can be used as water for extraction.

Then, a content of zinc in the obtained smithsonite extract is preferably 1.2 to 2.5 g/L and more preferably 1.5 to 2.0 g/L. When the content of zinc in the smithsonite extract is within the above range, body balance ability can be enhanced by virtue of synergy with another extract without producing precipitates even when the external composition for skin of the present invention is stored for a long time of several months, several years, or the like in its liquid state. The content of zinc is calculated according to a method in which a calibration curve is prepared from a zinc standard solution with a known concentration using atomic absorption spectrometry and a quantity is determined by the calibration curve method, or the like.

Further, a content of the smithsonite extract in the external composition for skin of the present invention is preferably 0.2 to 0.5% by weight and more preferably 0.3 to 0.4% by weight. When the content of the smithsonite extract in the external composition for skin is within the above range, body balance ability can be enhanced.

In addition, while the smithsonite extract can also be obtained by conducting the above-described extraction operations by one's own, a commercially available product can also be purchased. As a commercially available product, ZIN'CITE (manufactured by IKEDA CORPORATION) can be available, for example.

An olivine extract is an extract obtained from olivine, which is a nesosilicate mineral of magnesium and the like, through extraction with water. More specifically, the olivine extract is an aqueous solution which is a filtrate obtained by pulverizing raw olivine to approximately have a predetermined particle diameter, adding water and optionally an acidic compound, a solubilizing agent, and an antiseptic to the pulverized matter followed by stirring and mixing, and subsequently filtering the resulting mixture with a filter or the like. In addition to water at an ordinary temperature of about 20 to 30° C., cold water at a temperature lower than ordinary temperature and warm water and hot water at a temperature higher than ordinary temperature on the contrary can be used as water for extraction.

Then, a content of magnesium in the obtained olivine extract is preferably 2.0 to 4.5 g/L and more preferably 2.5 to 4.0 g/L. When the content of magnesium in the olivine extract is within the above range, body balance ability can be enhanced by virtue of synergy with another extract without producing precipitates even when the external composition for skin of the present invention is stored for a long time of several months, several years, or the like in its liquid state. The content of magnesium is calculated according to a method in which a calibration curve is prepared from a magnesium standard solution with a known concentration using atomic absorption spectrometry and a quantity is determined by the calibration curve method, or the like.

Further, a content of the olivine extract in the external composition for skin of the present invention is preferably 0.2 to 0.5% by weight and more preferably 0.3 to 0.4% by weight. When the content of the olivine extract in the external composition for skin is within the above range, body balance ability can be enhanced.

In addition, while the olivine extract can also be obtained by conducting the above-described extraction operations by one's own, a commercially available product can also be purchased. As a commercially available product, OLI'VINE (manufactured by IKEDA CORPORATION) can be available, for example.

Further, a surfactant can be optionally added. An oily compound which may be contained in each extract, which is an active ingredient of the external composition for skin, can be uniformly dissolved or dispersed by blending a surfactant. Examples of the surfactant include a cationic surfactant, an anionic surfactant, an ampholytic surfactant, and a nonionic surfactant.

The cationic surfactant is a surfactant which becomes a cation on dissociating in water, and an alkyl trimethyl ammonium salt, an alkyl dimethyl ammonium salt, an alkyl benzyl dimethyl ammonium salt, and the like are preferable, for example. Alkyl groups thereof preferably have 12 to 22 carbon atoms, and a counter anion thereof is preferably chloride ion, hydroxide ion, bromide ion, or the like.

Further, the anionic surfactant is a surfactant which becomes an anion on dissociating in water, and a fatty acid salt, a monoalkyl sulfate, an alkyl polyoxyethylene sulfate, an alkylbenzene sulfonate, monoalkyl phosphate, and the like are preferable, for example. Alkyl groups thereof preferably have 12 to 22 carbon atoms, and a counter cation thereof is preferably sodium ion, potassium ion, calcium ion, magnesium ion, or the like.

Further, the ampholytic surfactant is a surfactant which has both an anionic part and a cationic part in combination in a molecule and becomes a cation, an anion, and ampholytic including a cationic property and an anionic property depending on the pH of a solution, and an alkyl dimethyl amine oxide, an alkyl carboxybetaine, and the like are preferable, for example. Alkyl groups thereof preferably have 12 to 22 carbon atoms.

Further, the nonionic surfactant is an activator whose hydrophilic part has a hydrophilic site not being ionized, and polyoxyethylene alkyl ethers such as a polyoxyethylene cetyl ether and a polyoxyethylene stearyl ether; polyhydric alcohol fatty acid esters such as a glycerol fatty acid ester, a sorbitan fatty acid ester, and a sucrose fatty acid ester; polyoxyethylene adducts of polyhydric alcohol fatty acid esters; fatty acid diethanolamides and the like are preferable, for example. Among the above-described nonionic surfactants, surfactants having an HLB of 3 to 17 calculated according to Griffin's equation are more preferable. With respect to surfactants having a polyoxyethylene skeleton among the above-described nonionic surfactants, an addition mole number of oxyethylene can appropriately vary. Nonionic surfactants having an HLB within the above-range produce neither dreg nor precipitates even when the external composition for skin is stored for a long time and are excellent in storage stability.

In addition, an alcohol can be optionally blended in the external composition for skin of the present invention. Each extract which is an active ingredient of the external composition for skin can be uniformly dissolved or dispersed by blending an alcohol. As the alcohol, lower alcohols having 1 to 4 carbon atoms such as methanol, ethanol, n-propyl alcohol, isopropyl alcohol, and n-butyl alcohol are preferable, and ethanol, which can be also used for drugs and quasi-drugs, is more preferable. In addition, these alcohols can be used singly in combinations of two or more.

In addition, additional water can be blended in the external composition for skin of the present invention. By virtue of blending water, the concentration of each extract which is an active ingredient of the external composition for skin can be diluted, skin directly or indirectly contacting the external composition for skin can be prevented from suffering side effects such as inflammation, and other side effects which develop when the external composition flows into a blood flow through the skin can be prevented. Water to be used is preferably water according to Japanese Pharmacopoeia standards, and ordinary water including tap water, well water, and the like as well as purified water obtained by treating ordinary water through any one of distillation, ion-exchange treatment with an ion-exchange membrane, and ultrafiltration with an ultrafiltration membrane or a combination thereof, sterile purified water obtained by sterilization treatment of purified water through heating, etc., and the like are preferable, for example.

Further, a fulvic acid (humus extract), a bactericidal agent such as benzalkonium chloride and chlorhexidine gluconate, an antiseptic such as methylparaben, an antioxidant agent such as tocopherol, vitamin C, and BHT, moisturizing component such as glycerin, sodium hyaluronate, and chondroitin sulfate sodium, a perfume, a colorant, and the like can be optionally blended in the external composition for skin of the present invention in addition to the above components.

In addition, the external composition for skin of the present invention can be placed in a container capable of splaying or applying the external composition for skin and used by contacting the external composition for skin with the skin of an arm, a leg, a body trunk, or the like by directly spraying or applying the external composition for skin. Further, the external composition for skin of the present invention can also be used by impregnating a corset, a wristband, clothes, or the like to be attached to a body with the external composition for skin through spraying or application and gradually bringing the external composition for skin into indirect contact with the skin of an arm, a leg, a body trunk, or the like.

EXAMPLES

Example 1

An external composition for skin was produced by blending 0.35% by weight of a rhodochrosite extract ("RHODO'LITE 2" manufactured by IKEDA CORPORATION, manganese content: 1.93 g/L), which is a water extract of rhodochrosite, 0.35% by weight of a hematite extract ("HEMA'TITE" manufactured by IKEDA CORPORATION, iron content: 0.6 g/100 g), which is a water extract of hematite, 0.35% by weight of a smithsonite extract ("ZIN'CITE" manufactured by IKEDA CORPORATION, zinc content: 1.9 g/L), which is a water extract of smithsonite, 0.35% by weight of an olivine extract ("OLI'VINE" manufactured by IKEDA CORPORATION, magnesium content: 3.2 g/L), which is a water extract of olivine, 0.35% by weight of a humus extract ("FX21 Dogyanna" manufactured by Japan Humin Kagaku CO., LTD.), 0.15% by weight of methylparaben, 7% by weight of ethanol, and 91.9% by weight of water to prepare a composition of 100% by weight, and stirring and uniformly mixing the resulting composition at a temperature of 30° C. for a predetermined time.

Comparative Example 1

An external composition for skin was produced in the same manner as Example 1 except that no rhodochrosite extract was blended and the blending ratio of water was changed to 91.45% by weight.

Comparative Example 2

An external composition for skin was produced in the same manner as Example 1 except that no hematite extract was blended and the blending ratio of water was changed to 91.45% by weight.

Comparative Example 3

An external composition for skin was produced in the same manner as Example 1 except that no smithsonite extract was blended and the blending ratio of water was changed to 91.45% by weight.

Comparative Example 4

An external composition for skin was produced in the same manner as Example 1 except that no olivine extract was blended and the blending ratio of water was changed to 91.45% by weight.

Test of Amount of Nitric Oxide (NO) in Blood

Performance of each of the external compositions for skin of the Example and Comparative Examples produced as described above was evaluated in terms of change in concentration of nitric oxide in blood in a living body. Specifically, a catheter-type nitric oxide censor was inserted to the hepatic portal vein of a rat under anesthesia, then a cloth to which each of the external compositions for skin of Example and Comparative Examples had been applied at a predetermined amount and which had been dried was contacted with the chest and the abdomen of the rat, and the concentration of nitric oxide in blood was measured using an electrochemical measurement device (IMEC-601 manufactured by Inter Medical Co., Ltd.) over time. Results thereof are shown in FIG. 1. In each chart of FIG. 1, the horizontal axis is measurement time (minutes) and the vertical axis is an amount of nitric oxide in blood, with a point closer to the upper end on the vertical axis representing a larger amount of nitric oxide in blood.

As shown in FIG. 1, it has been found that when the cloth to which the external composition for skin has been applied at a predetermined amount and which has been dried is attached to a rat two minutes after the starting of the measurement (the time point marked with an arrow), the amount of nitric oxide in blood increases at about two and a half minutes after the starting of the measurement (about 30 seconds after the attachment) in Example 1. However, the amounts of nitric oxide in blood are not clearly increased in Comparative Examples 1 to 4. From these results, it has been found that an effect of promptly increasing an amount of nitric oxide in blood is exerted when all four kinds of the rhodochrosite extract, hematite extract, smithsonite extract, and olivine extract are contained. Since nitric oxide is generally known to act on smooth muscles to serve to dilate blood vessels in a living body, it is also suggested that vasodilatation is caused in a living body.

Test of Body Temperature Change

Figure 2:
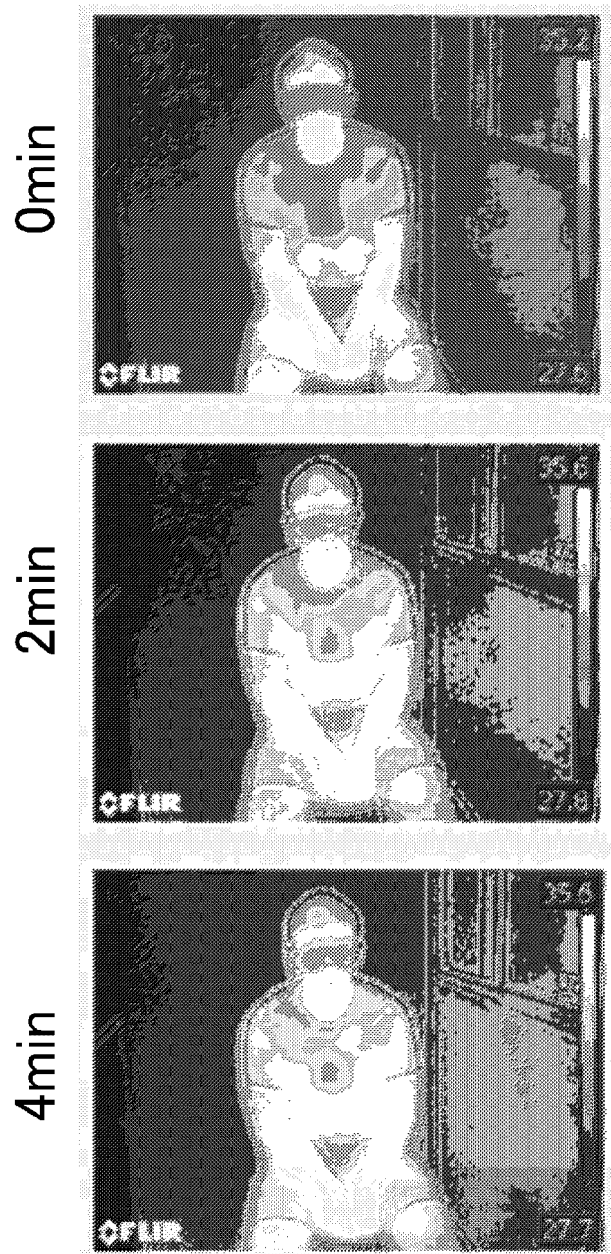
FIG. 2 shows views showing test results of measurements of changes in body temperature of a subject wearing a shirt impregnated with the composition of Example 1.
Figure 3:
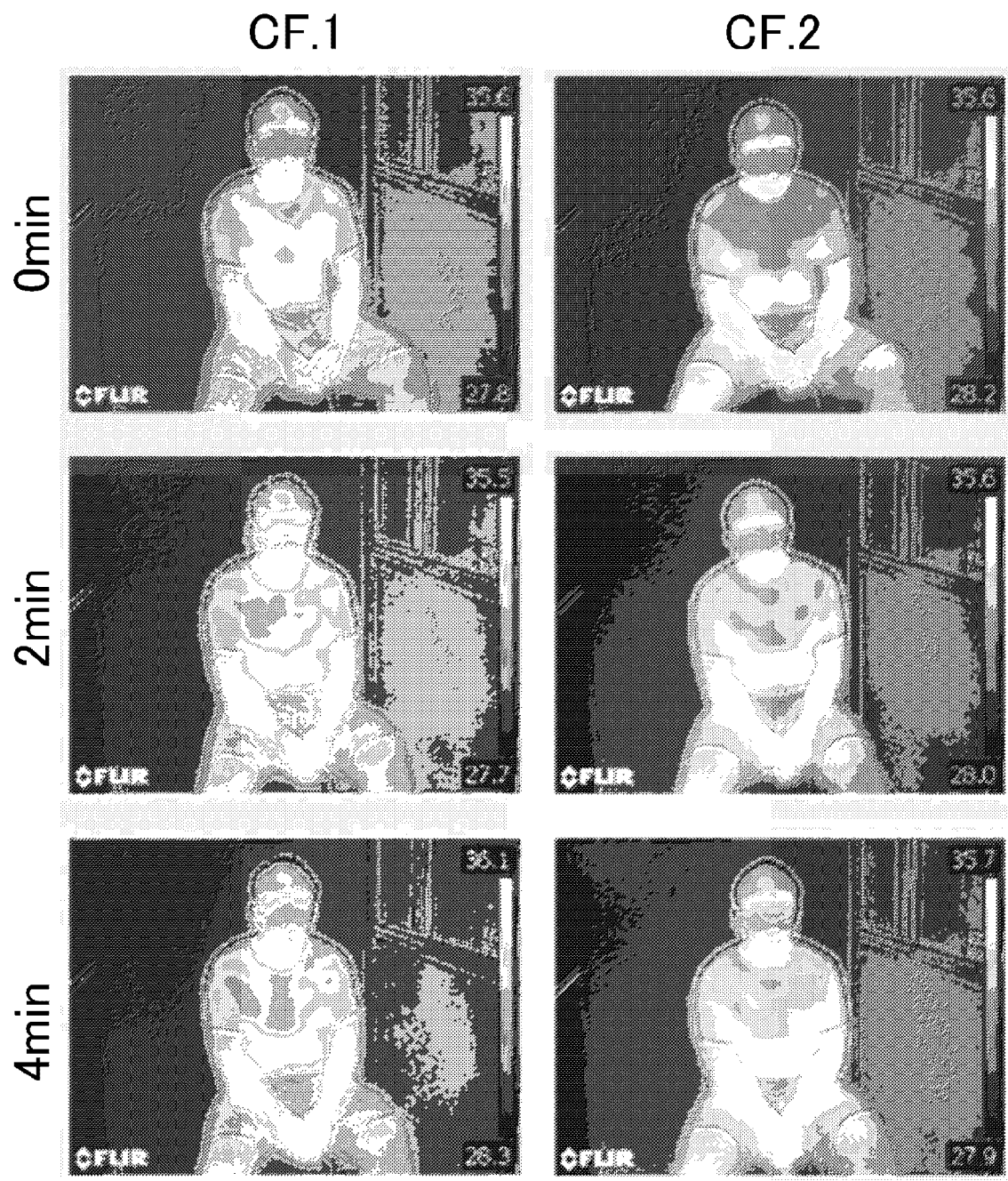
FIG. 3 shows views showing test results of measurements of changes in body temperature of subjects wearing shirts impregnated with the compositions of Comparative Example 1 and Comparative Example 2 respectively.
Figure 4:
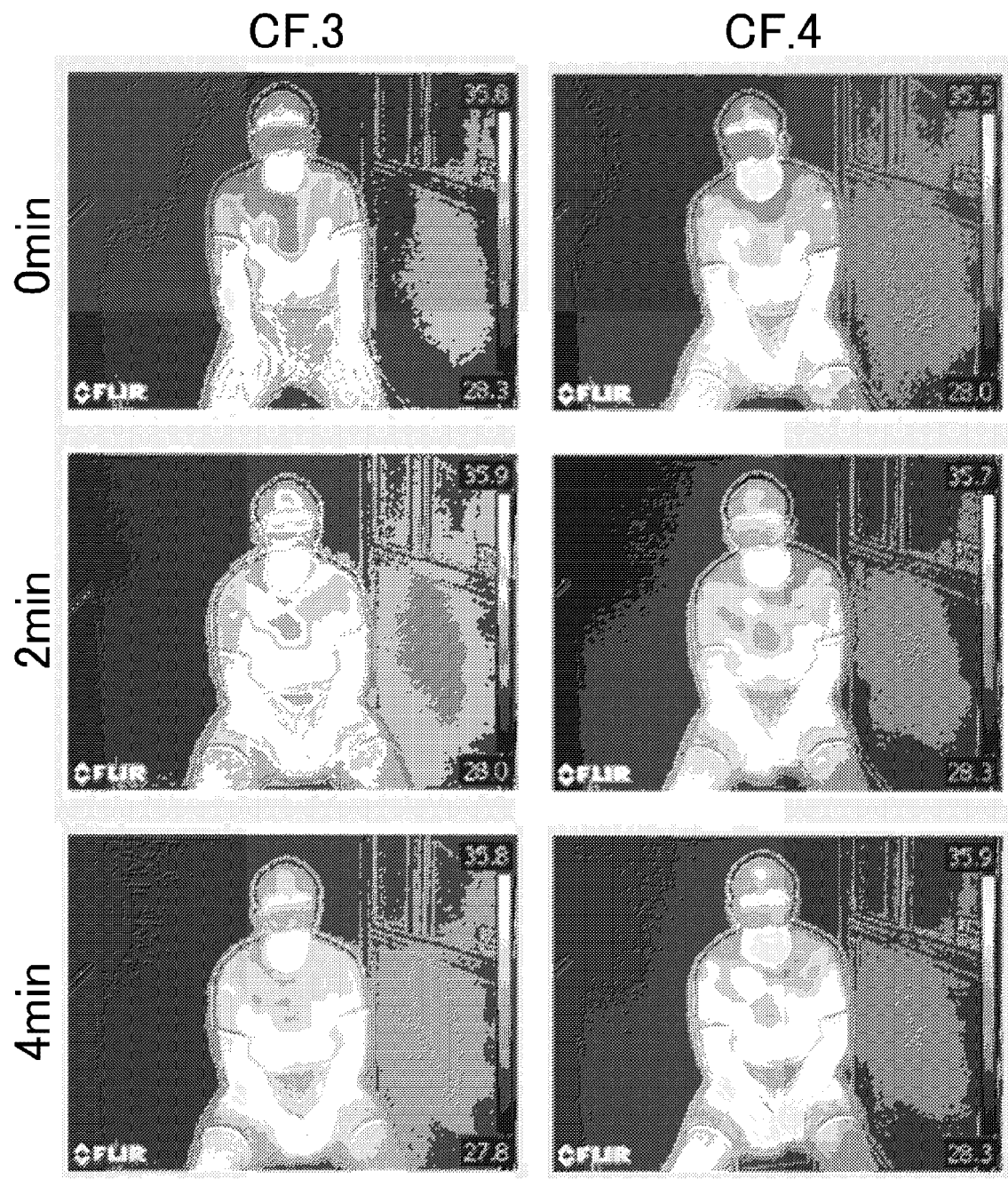
FIG. 4 shows views showing test results of measurements of changes in body temperature of subjects wearing shirts impregnated with the compositions of Comparative Example 3 and Comparative Example 4 respectively.

Performance of each of the external compositions for skin of the Example and Comparative Examples produced as described above was evaluated in terms of change in body temperature of a living body. Specifically, after a human subject wore a shirt to which each of the external compositions for skin of Example and Comparative Examples had been applied at a predetermined amount and which had been dried, change in body temperature was measured over time using a portable thermography camera (FLIR C2). Thermographs showing the body temperature immediately after, two minutes after, and four minutes after the wearing of the shirt are shown in FIG. 2 to FIG. 4. The subject in every test is the same person.

As shown in FIG. 2, it has been found that the temperature around the breast and shoulders of the subject increases with the lapse of time, after the lapse of two minutes and four minutes in Example 1. However, as shown in FIG. 3 and FIG. 4, the temperature around the breast and shoulders of the subject does not increase or increases not as much as Example 1 with the lapse of time in Comparative Examples 1 to 4. From these results, it has been found that an effect of increasing body temperature of a subject to the highest level is exerted when all four kinds of the rhodochrosite extract, hematite extract, smithsonite extract, and olivine extract are contained. In view of the results of the amount of nitric oxide in a living body described above, it is inferred that blood vessels dilate through the action of nitric oxide generated in a living body to increase a blood flow rate and increase body surface temperature.

Body Balance Test 1

Figure 5:
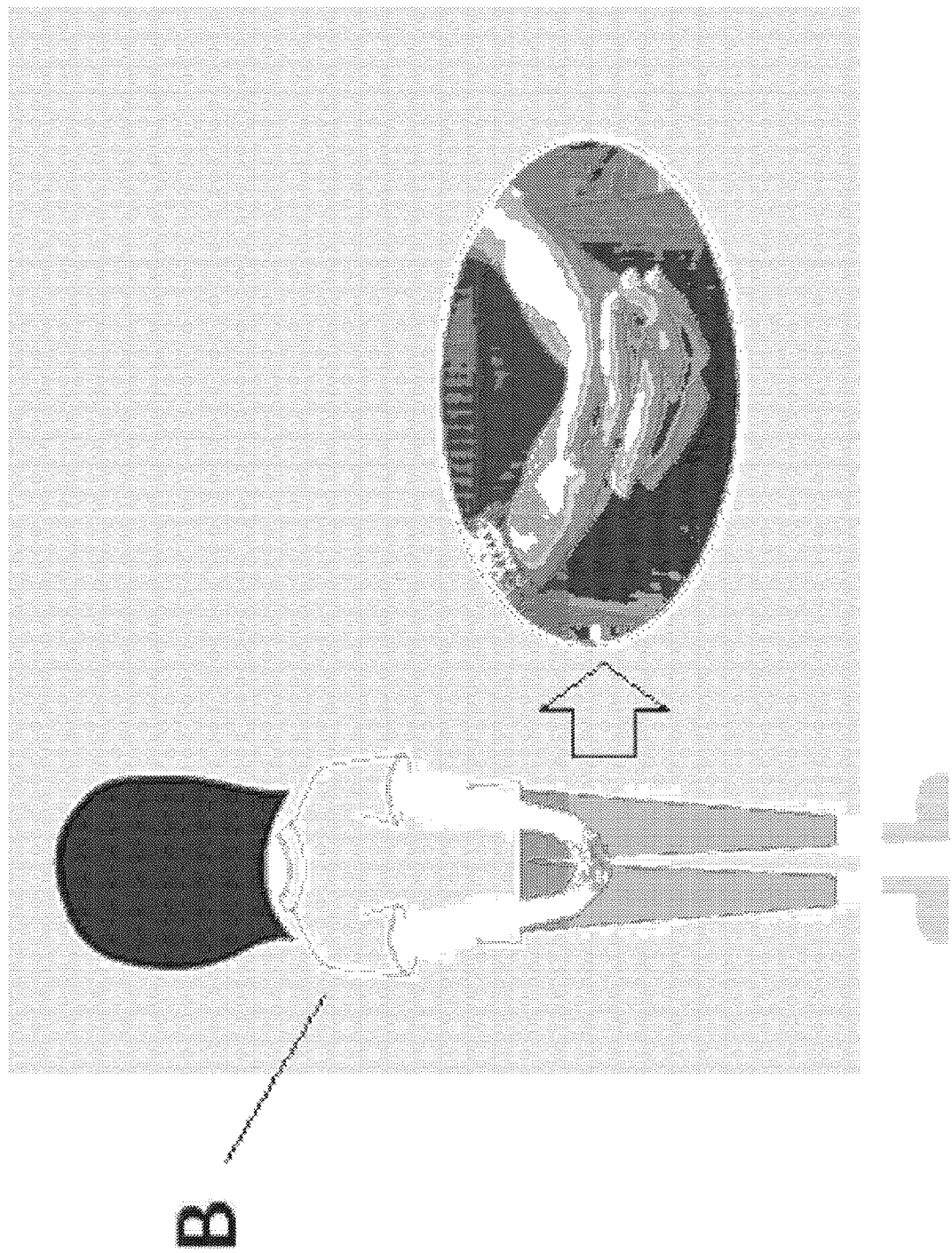
FIG. 5 is an illustration illustrating a state where a subject is preparing for evaluation of an external composition for skin of the present invention.
Figure 6:
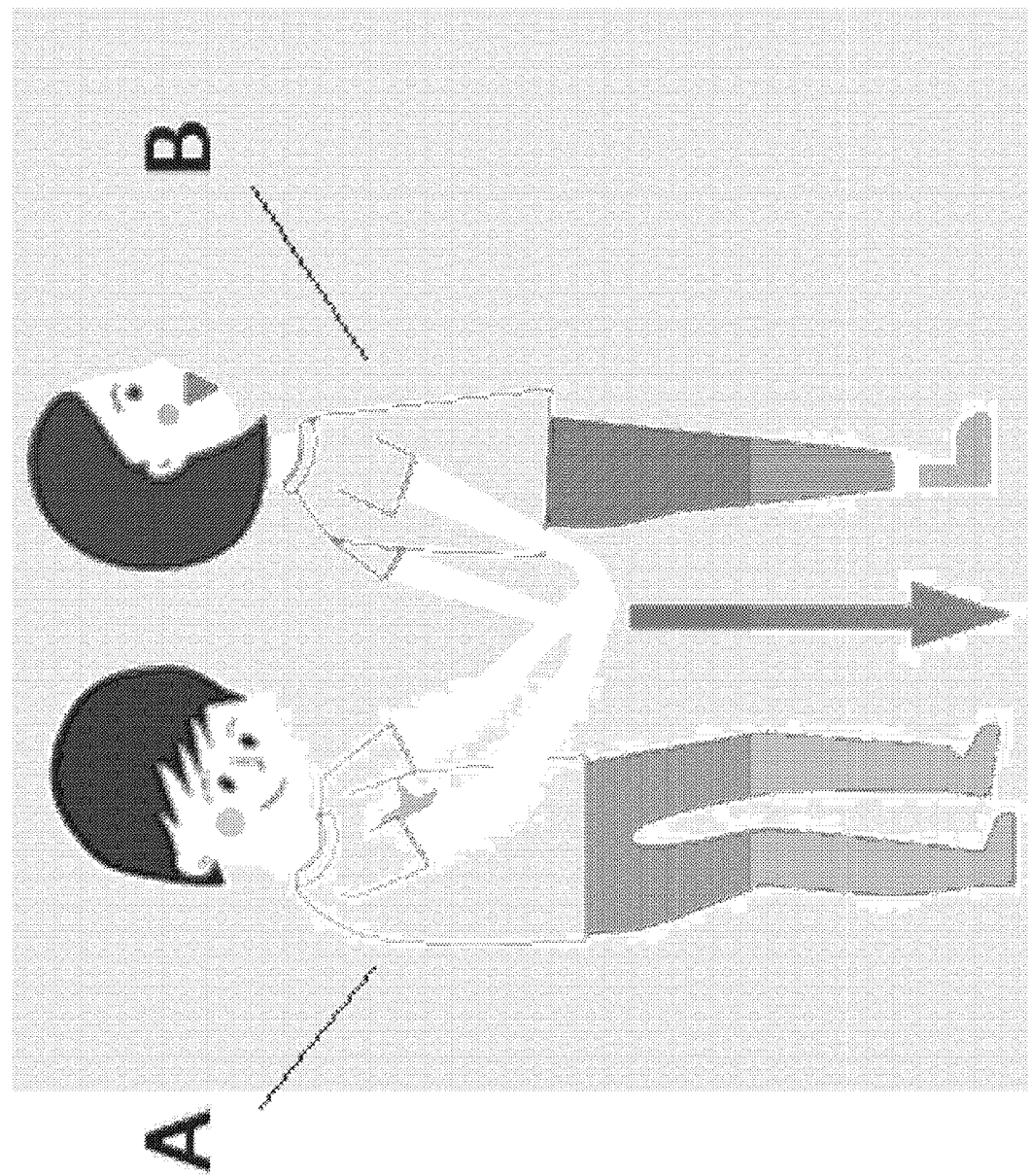
FIG. 6 is an illustration illustrating a state where a subject is tested by a tester for evaluation of an external composition for skin of the present invention.

Performance of each of the external compositions for skin of the Example and Comparative Examples produced as described above was evaluated in terms of body balance keeping ability pertaining to lack of balance when force was applied to a body. Specifically, six healthy adult males and females including a female aged 58 years, a female aged 45 years, a female aged 25 years, a male aged 42 years, a male aged 29 years, and a male aged 28 years each wearing a corset, which had been impregnated with each of the prepared external compositions for skin and wound around the waist, stood in a stable state for several minutes first. Then, a subject B interlocked his/her hands behinds his/her back as shown in FIG. 5, and a tester A pushed the hands of the subject B downward in the vertical direction with a predetermined force as shown in FIG. 6 to evaluate the extent of lack of balance as the body balance keeping ability. A situation in which the both feet of the subject B did not take even one step when the tester A pushed the hands of the subject B down was classified as good, a situation in which the both feet of the subject B took one step was classified as fair, and a situation in which the both feet of the subject B took two or more steps was classified as fair, and "good" was evaluated as being preferable and "fair" and "poor" were evaluated as not being preferable. The above test was conducted in a double-blind test method, that is, the test was conducted under the situation in which both of the tester A and the subject B did not know whether the used composition corresponded to Example or any of Comparative Examples.

Body Balance Test 2

Performance of each of the external compositions for skin of the Example and Comparative Examples produced as described above was evaluated in terms of body balance keeping ability pertaining to whether a subject could keep standing for a predetermined time when the subject was blindfolded and stood on one foot. Specifically, each of 22 subjects of males and females aged 18 to 22 years each wearing a shirt to which each of the external compositions for skin of Example and Comparative Examples had been applied at a predetermined amount and which had been dried wore an eye mask, stood on one foot with his/her right food grounded, and stayed for 20 seconds. Then, the number of subjects who lost their balance and grounded their raised feet was counted during this period of 20 seconds. Subjects were not informed of the distinction between Example and Comparative Examples in order to prevent the influence of placebo effect.

The blending ratios of the blended components in respective compositions according to Example 1 and Comparative Examples 1 to 4 and performance evaluation results thereof in terms of body balance 1 and body balance 2 are shown in Table 1 and Table 2.

Such an effect of allowing body balance to be easily kept is thought to be exerted as follows. The mineral components contained in the rhodochrosite extract, hematite extract, smithsonite extract, and olivine extract in the composition penetrate from the integument of skin to act on a substance (EDRF: endothelium-derived relaxing factor) which relaxes muscles lying inside blood vessels, enhance the ability to synthesize nitric oxide (NO), dilate blood vessels, and promote a blood flow. Then, censors called "muscle spindle" and "tendon organ" within muscles and tendons of a body are stimulated by the dilation of blood vessels and promotion of a blood flow. Information such as distortion of a body and contraction of a muscle and a tendon at that time is instantly transmitted from a terminal nerve to the brain, and an instruction to keep body balance is provided from the brain. While such a working mechanism has not been completely defined yet, such a working mechanism is thought to be highly valid in view of results of the above-described test of the amount of nitric oxide (NO) in blood and the test of body temperature change obtained through verifications conducted by research institutions such as a university.

The invention claimed is:

1. An external composition for skin, the external composition for skin comprising:

0.2 to 0.5% by weight of a rhodochrosite extract extracted from rhodochrosite with water, 0.2 to 0.5% by weight of a hematite extract extracted from hematite with water, 0.2 to 0.5% by weight of a smithsonite extract extracted from smithsonite with water, and

TABLE 1

| | | Example | Comparative Examples | | | |
|---|---|---|---|---|---|---|
| | | EX1 | CF1 | CF2 | CF3 | CF4 |
| Composition | Rhodochrosite extract (wt %) | 0.35 | | 0.35 | 0.35 | 0.35 |
| | Hematite extract (wt %) | 0.35 | 0.35 | | 0.35 | 0.35 |
| | Smithsonite extract (wt %) | 0.35 | 0.35 | 0.35 | | 0.35 |
| | Olivine extract (wt %) | 0.35 | 0.35 | 0.35 | 0.35 | |
| | Humus extract (wt %) | 0.35 | 0.35 | 0.35 | 0.35 | 0.35 |
| | Methylparaben (wt %) | 0.15 | 0.15 | 0.15 | 0.15 | 0.15 |
| | Water (wt %) | 91.1 | 91.45 | 91.45 | 91.45 | 91.45 |
| | Ethanol (wt %) | 7 | 7 | 7 | 7 | 7 |
| | Total (wt %) | 100 | 100 | 100 | 100 | 100 |
| Performance evaluation | Body balance Female aged 58 years | Good | Poor | Poor | Poor | Poor |
| | Female aged 45 years | Good | Poor | Poor | Poor | Poor |
| | Female aged 25 years | Good | Poor | Poor | Poor | Poor |
| | Female aged 42 years | Good | Poor | Poor | Poor | Poor |
| | Male aged 29 years | Good | Poor | Poor | Poor | Poor |
| | Male aged 28 years | Good | Poor | Poor | Poor | Poor |

TABLE 2

| | | | Example | Comparative Examples | | | |
|---|---|---|---|---|---|---|---|
| | | | EX1 | CF1 | CF2 | CF3 | CF4 |
| Performance evaluation | Body balance | Landing of foot (headcount) | 3 | 7 | 8 | 9 | 10 |
| | | Landing of foot (%) | 14 | 32 | 36 | 41 | 45 |

As shown in Table 1 and Table 2, it has been surprisingly found that a composition containing all four kinds of the rhodochrosite extract, hematite extract, smithsonite extract, and olivine extract has an effect of allowing body balance to be easily kept with a significant difference.

0.2 to 0.5% by weight of an olivine extract extracted from olivine with water, wherein a content of manganese in the rhodochrosite extract is 1.0 to 3.5 g/L, a content of iron in the hematite extract is 0.2 to 1.2 g/100 g, a content of zinc in the smithsonite extract is 1.2 to 2.5 g/L, and a content of magnesium in the olivine extract is 2.0 to 4.5 g/L.

2. A method of dilating a blood vessel, the method comprising:

provising an external composition comprising:

0.2 to 0.5% by weight of a rhodochrosite extract extracted from rhodochrosite with water, 0.2 to 0.5% by weight of a hematite extract extracted from hematite with water, 0.2 to 0.5% by weight of a smithsonite extract extracted from smithsonite with water, and 0.2 to 0.5% by weight of an olivine extract extracted from olivine with water, wherein a content of manganese in the rhodochrosite extract is 1.0 to 3.5 g/L, a content of iron in the hematite extract is 0.2 to 1.2 g/100 g, a content of zinc in the smithsonite extract is 1.2 to 2.5 g/L, and a content of magnesium in the olivine extract is 2.0 to 4.5 g/L; and applying said external composition to skin under conditions effective to dilate a blood vessel.

3. A method of enhancing balance ability, the method comprising:

providing an external composition comprising:

0.2 to 0.5% by weight of a rhodochrosite extract extracted from rhodochrosite with water, 0.2 to 0.5% by weight of a hematite extract extracted from hematite with water, 0.2 to 0.5% by weight of a smithsonite extract extracted from smithsonite with water, and 0.2 to 0.5% by weight of an olivine extract extracted from olivine with water, wherein a content of manganese in the rhodochrosite extract is 1.0 to 3.5 g/L, a content of iron in the hematite extract is 0.2 to 1.2 g/100 g, a content of zinc in the smithsonite extract is 1.2 to 2.5 g/L, and a content of magnesium in the olivine extract is 2.0 to 4.5 g/L; and applying said external composition to skin under conditions effective to enhance balance ability.

4. A method of increasing an amount of nitric oxide in blood, the method comprising:

providing an external composition comprising:

0.2 to 0.5% by weight of a rhodochrosite extract extracted from rhodochrosite with water, 0.2 to 0.5% by weight of a hematite extract extracted from hematite with water, 0.2 to 0.5% by weight of a smithsonite extract extracted from smithsonite with water, and 0.2 to 0.5% by weight of an olivine extract extracted from olivine with water, wherein a content of manganese in the rhodochrosite extract is 1.0 to 3.5 g/L, a content of iron in the hematite extract is 0.2 to 1.2 g/100 g, a content of zinc in the smithsonite extract is 1.2 to 2.5 g/L, and a content of magnesium in the olivine extract is 2.0 to 4.5 g/L; and applying said external composition to skin under conditions effective to increase an amount of nitric oxide in blood.

\* \* \* \* \*